United States Patent

Steinmann

[11] Patent Number: 5,998,518
[45] Date of Patent: Dec. 7, 1999

[54] PHENYL GLYCIDYL ETHER HALS

[75] Inventor: Alfred Steinmann, Praroman, Switzerland

[73] Assignee: Ciba Specialty Chemcials Corporation, Tarrytown, N.Y.

[21] Appl. No.: 08/950,617

[22] Filed: Oct. 15, 1997

[30] Foreign Application Priority Data

Oct. 16, 1996 [CH] Switzerland ............... 2524/96

[51] Int. Cl.⁶ .................................. C08J 5/3435
[52] U.S. Cl. .................. 524/99; 526/265; 526/273; 526/347.1; 549/545; 549/555; 549/560
[58] Field of Search .................. 549/545, 555, 549/560; 526/265, 273, 347.1; 524/99

[56] References Cited

U.S. PATENT DOCUMENTS

| | | | |
|---|---|---|---|
| 3,847,930 | 11/1974 | Randell | 252/401 |
| 4,038,280 | 7/1977 | Randell | 252/402 |
| 4,413,076 | 11/1983 | Soma et al. | |
| 4,460,725 | 7/1984 | Leistner et al. | |
| 4,537,923 | 8/1985 | Slongo et al. | |
| 5,420,204 | 5/1995 | Valet et al. | |
| 5,457,204 | 10/1995 | Steinmann | |
| 5,521,282 | 5/1996 | Steinmann | 528/419 |
| 5,616,637 | 4/1997 | Steinmann | 524/102 |
| 5,719,257 | 2/1998 | Steinmann | 528/367 |

OTHER PUBLICATIONS

Luston and Vass, Makromolekulare Chemie, Macromol. Symp. 27, 231(1989).

Primary Examiner—Robert Dawson
Assistant Examiner—D. Aylward
Attorney, Agent, or Firm—Luther A. R. Hall

[57] ABSTRACT

A description is given of compounds of the formula I

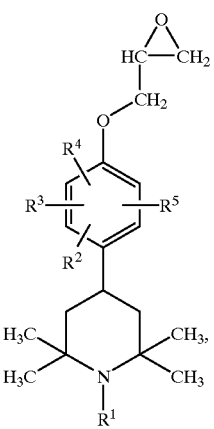

(I)

where
$R^1$ is H, $C_1$–$C_{12}$alkyl, $C_2$–$C_{12}$alkenyl, $C_2$–$C_{12}$alkynyl, O—$C_1$–$C_{12}$alkyl, CO—$C_1$–$C_{12}$alkyl, in which radicals alkyl chains may also be interrupted by O, S, S=O, $SO_2$ or N—$C_1$–$C_{12}$alkyl, or is $C_5$–$C_{12}$cycloalkyl which is unsubstituted or substituted by
 1 to 4 $C_1$–$C_4$alkyl and/or $C_1$–$C_4$alkoxy radicals, O—$C_5$–$C_{12}$cycloalkyl, which is unsubstituted or substituted by 1 to 4 $C_1$–$C_4$alkyl and/or $C_1$–$C_4$alkoxy radicals, CO—$C_6$–$C_{14}$aryl, which is unsubstituted or substituted by 1 to 9 $C_1$–$C_4$alkyl and/or
 $C_1$–$C_4$alkoxy radicals, O-benzyl, which on the aromatic ring is unsubstituted or substituted by 1 to 4 $C_1$–$C_4$alkyl and/or $C_1$–$C_4$alkoxy radicals, CO-benzyl, which on the aromatic ring is unsubstituted or substituted by 1 to 4 $C_1$–$C_4$alkyl and/or $C_1$–$C_4$alkoxy radicals, and
$R^2$, $R^3$, $R^4$ and $R^5$ independently of one another are H, $C_1$–$C_{12}$alkyl, $C_5$–$C_{12}$cycloalkyl, O—$C_1$–$C_{12}$alkyl, O-phenyl, halogen or $NO_2$
and the homopolymers, copolymers and terpolymers thereof, and the reaction products with at least one other monoglycidyl compound, not of the formula I, or with an amine or with a carboxylic acid or with a phenol or dicarboxylic anhydride or alcoholate, and compounds in which one or more compounds of the formula I is or are adsorbed on a filler such as $TiO_2$, $SiO_2$, $CaCO_3$, $CaSO_4$, $BaSO_4$, $Al(OH)_3$, talc, carbon black, glass fibres or glass beads, cellulose or wood flour.

30 Claims, No Drawings

PHENYL GLYCIDYL ETHER HALS

The invention relates to novel 4-[4-(2,3-epoxypropoxy) phenyl]-2,2,6,6-tetramethylpiperidines which may carry substituents on the ring nitrogen and on the phenylene ring, to their homopolymers, copolymers and terpolymers, to their use for stabilizing organic material against damage by light, oxygen and/or heat, and to organic material stabilized with these compounds or polymers.

The preparation of some compounds of the 4-(2,3-epoxypropoxy)-2,2,6,6-tetramethylpiperidine[4-epoxy-HALS] and their use as stabilizers for organic polymers are described, for example, by Luston and Vass, Makromolekulare Chemie, Macromol. Symp. 27, 231 (1989).

Reaction products of these epoxides with toluenesulfonic acid and ethylenedisulfonic acid, and their combined use as curing catalysts and light stabilizers in coating materials, are mentioned in EP-A-0 097 616.

The binding of reactive alkylpiperidines onto fluoropolymers which contain free carboxyl groups is described in EP-A-526 399.

The publication EP-A-001 835 discloses the further reaction of the piperidines which contain epoxide groups with dicarboxylic anhydrides to give polyesters.

U.S. Pat. No. 5,521,282 describes the anionic polymerization of 4-(2,3-epoxypropoxy)-2,2,6,6-tetramethylpiperidines to give polyethers having hindered amine side chains and their use as stabilizers. The poly (glycidyl ether HALS) predominantly have a softening temperature which is below 20° C.; in other words, the products of their preparation are for the most part resins.

Thus there continues to be a need for new stabilizers of the HALS type which are solid at room temperature and have improved service properties, including in particular better thermal stability than the compounds specified in U.S. Pat. No. 5,521,282.

It has now been found that certain compounds of the 4-[4-(2,3-epoxypropoxy)phenyl]-2,2,6,6-tetramethylpiperidine type are surprisingly suitable as stabilizers for organic material. In addition they have a high temperature resistance and therefore permit higher processing temperatures in use and thus a higher throughput in the course of subsequent processing of the products stabilized in this way.

The invention therefore initially provides compounds of the formula I

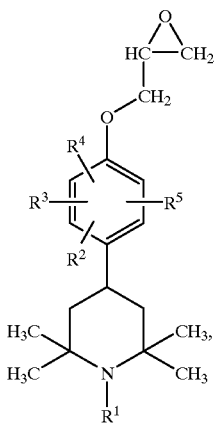

(I)

where
$R^1$ is H, $C_1$–$C_{12}$alkyl, $C_2$–$C_{12}$alkenyl, $C_2$–$C_{12}$alkynyl, O—$C_1$–$C_{12}$alkyl, CO—$C_1$–$C_{12}$alkyl, in which radicals alkyl chains may also be interrupted by O, S, S=O, $SO_2$ or N—$C_1$–$C_{12}$alkyl, or is $C_5$–$C_{12}$cycloalkyl which is unsubstituted or substituted by 1 to 4 $C_1$–$C_4$alkyl and/or $C_1$–$C_4$alkoxy radicals, O—$C_5$–$C_{12}$cycloalkyl, which is unsubstituted or substituted by 1 to 4 $C_1$–$C_4$alkyl and/or $C_1$–$C_4$alkoxy radicals, CO—$C_6$–$C_{14}$aryl, which is unsubstituted or substituted by 1 to 9 $C_1$–$C_4$alkyl and/or $C_1$–$C_4$alkoxy radicals, O-benzyl, which on the aromatic ring is unsubstituted or substituted by 1 to 4 $C_1$–$C_4$alkyl and/or $C_1$–$C_4$alkoxy radicals, CO-benzyl, which on the aromatic ring is unsubstituted or substituted by 1 to 4 $C_1$–$C_4$alkyl and/or $C_1$–$C_4$alkoxy radicals, and $R^2$, $R^3$, $R^4$ and $R^5$ independently of one another are H, $C_1$–$C_{12}$alkyl, $C_5$–$C_{12}$cycloalkyl, O—$C_1$–$C_{12}$alkyl, O-phenyl, halogen or $NO_2$.

$R^1$, $R^2$, $R^3$, $R^4$ and $R^5$ as $C_1$–$C_{12}$alkyl can be straight-chain or branched and are, for example, methyl, ethyl, propyl, isopropyl, n-butyl, sec-butyl, isobutyl, t-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl. The alkyl group $R^1$ has in particular 1 to 8, preferably 1 to 4 C atoms. The alkyl groups $R^2$, $R^3$, $R^4$ and $R^5$ have in particular 1 to 6 C atoms.

Preferably 2, especially 3 of the substituents $R^2$ $R^3$, $R^4$ and $R^5$ are hydrogen.

$R_1$ as $C_2$–$C_{12}$alkenyl is, for example, vinyl, 1-propenyl, 2-propenyl, 1-butenyl, 2-butenyl, 3-butenyl and so on. Preference is given to alkenyl groups having 2 to 8 C atoms, especially those having 2 to 4 C atoms.

$R^1$ as $C_2$–$C_{12}$alkynyl is, for example, ethynyl, 1-propynyl, 2-propynyl, 1-butynyl, 2-butynyl, 3-butynyl and so on. Such alkynyl groups preferably have 2 to 8 C atoms, with particular preference being given to those having 2 to 4 C atoms.

The abovementioned alkyl chains can also be interrupted by O, S, S=O, $SO_2$ or N—$C_1$–$C_{12}$alkyl.

$R^1$ as $C_5$–$C_{12}$cycloalkyl is, for example, cyclopentyl, cyclohexyl, cycloheptyl and cyclooctyl and so on. Cyclohexyl is preferred. If cycloalkyl is substituted it carries preferably 2, in particular 1 substituent(s).

$C_6$–$C_{14}$aryl is, for example, phenyl, naphthyl, anthracenyl or phenanthrenyl. Phenyl is preferred.

$R^2$, $R^3$, $R^4$ and $R^5$ as halogen are F, Cl, Br or I, preferably Cl or Br, but especially Cl.

Particular preference is given to compounds of the formula I, where $R^1$ is H, $C_1$–$C_4$alkyl, $C_2$–$C_8$alkenyl, $C_2$–$C_4$alkynyl, O—$C_1$–$C_4$alkyl, CO—$C_1$–$C_4$alkyl or O—$C_5$–$C_6$cycloalkyl.

Particular preference is given to compounds of the formula I, in which $R^1$ is H, $C_1$–$C_{12}$alkyl, $C_2$–$C_{12}$alkenyl, $C_2$–$C_{12}$alkynyl, CO—$C_1$–$C_{12}$alkyl, where alkyl chains in these radicals can also be interrupted by O, S, S=O, $SO_2$ or N—$C_1$–$C_{12}$alkyl, and $R^2$, $R^3$, $R^4$ and $R^5$ independently of one another are H, $C_1$–$C_{12}$alkyl or O—$C_1$–$C_{12}$alkyl.

Especial preference is given to compounds of the formula I, in which $R^1$ is H, $CH_3$, $CH_2$—C≡CH or CO—$CH_3$ and $R^2$, $R^3$, $R^4$ and $R^5$ independently of one another are H or $CH_3$.

The invention also provides homopolymers, copolymers and terpolymers obtainable by anionic polymerization of one or more compounds of the formula I.

Such novel homopolymers, copolymers and terpolymers are preferably of the formula II

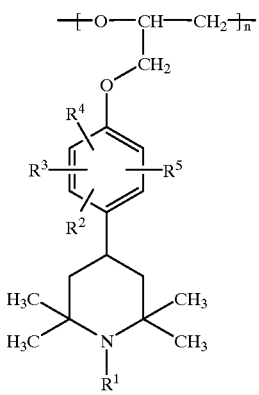

(II)

in which $R^1$, $R^2$, $R^3$, $R^4$ and $R^5$ are as defined for formula I and n is a number from 2 to 1000, and in which the general symbols in each repeating unit are identical or different.

n in the compounds of the formula II is preferably from 5 to 500, in particular from 5 to 100.

The invention also provides compounds obtainable by reacting compounds of the formula I with at least one other glycidyl compound not of the formula I, such as, for example, aliphatic or cycloaliphatic glycidyl ethers, for example n-butyl glycidyl ether or cyclohexyl glycidyl ether, or with a glycidyl ether-piperidine compound, as described, for example, in U.S. Pat. No. 5,521,282.

The invention provides, furthermore, compounds obtainable by reacting one or more compounds of the formula I with at least one amine or one carboxylic acid or one phenol or dicarboxylic anhydride or alcoholate.

Examples thereof are compounds obtainable by reacting compounds of the formula I with piperidines, alkylamines, polyalkylenepolyamines, polyaminoamides, polyoxyalkylenepolyamines, aromatic amines or triazine containing nucleophilic amino groups, aminocarboxylic acids or ammonia, with preference being given to piperidines which contain at least two nitrogen atoms and to polyoxyalkylenepolyamines which comprise amine-terminated polyethylene glycol or polypropylene glycol or both polyalkylene glycols, aromatic amines having not more than 2 aromatic carbon rings, triazine which is substituted on the C atoms by amino groups or substituents containing amino groups, aromatic aminocarboxylic acids or ammonia.

Preference is given to piperidines of the formula III

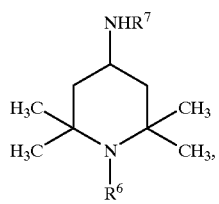

(III)

where
$R^6$ is H, $C_1$–$C_{12}$alkyl, $C_2$–$C_{12}$alkenyl, $C_2$–$C_{12}$alkynyl, $C_6$–$C_{20}$aryl, $C_7$–$C_{20}$aralkyl, O—$C_1$–$C_{12}$alkyl, O—$C_5$–$C_8$cycloalkyl, CO—$C_1$–$C_{12}$alkyl, CO—$C_6$–$C_{20}$aryl, CO—$C_7$–$C_{20}$aralkyl, O—CO—$C_1$–$C_{12}$alkyl or $C_1$–$C_6$alkyl-Z—$C_1$–$C_6$alkyl, where Z is O, S or C=O, and $R^7$ is H, $C_1$–$C_{12}$alkyl or

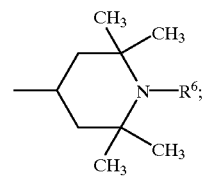

or alkylamines or dialkylamines containing not more than 20 C atoms; polyamines of the formulae IV to VI $$R^8HN\text{---}(CR^9R^{10})_n\text{---}[\text{---}NR^{11}\text{---}(CR^{12}R^{13})_n\text{---}]_a\text{---}NHR^{14},$$ (IV)

where $R^8$ to $R^{14}$ independently of one another are H, $CH_3$, $C_2H_5$ or $C_3H_7$, and $R^{11}$ can additionally be $R^8HN\text{---}(CR^9R^{10})_n$, n is 2 to 20 and a is 0 to 30,

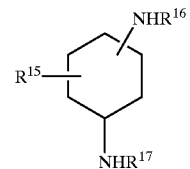

(V)

where $R^{15}$ to $R^{17}$ independently of one another are H, $CH_3$ or

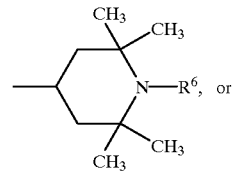, or

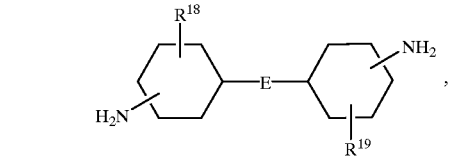

(VI)

where

E is a direct bond or $CH_2$, $C(CH_3)_2$, C=O, N—H, S, SO, $SO_2$ or O, and $R^{18}$ and $R^{19}$ independently of one another are H, $CH_3$ or

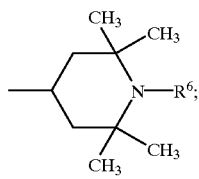

polyaminoamides of the formula VII

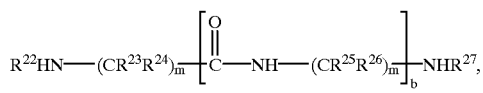
(VII)

where
$R^{22}$ to $R^{27}$ independently of one another are H or $CH_3$,
m is 1 to 20 and
b is 1 to 30;
polyoxyalkylenepolyamines of the formula VIII

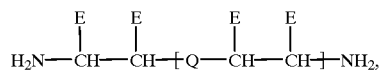
(VIII)

where
E independently at each occurrence is H or $CH_3$, and
Q independently at each occurrence is O or NH, and
c is 1 to 10,000;
aromatic amines of the formula IX

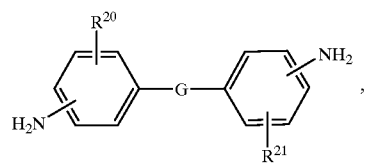
(IX)

where
G is a direct bond or $CH_2$, $C(CH_3)_2$, C=O, N—H, S, SO, $SO_2$ or O, and
$R^{20}$ and $R^{21}$ independently of one another are H, $CH_3$ or $C_2H_5$;
substituted triazines of the formula X

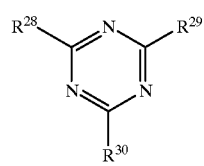
(X)

where
$R^{28}$ to $R^{30}$ independently of one another are substituents which contain a primary and/or secondary amine radical and which have a C number of from 1 to 18;

aminocarboxylic acids of the formula XI

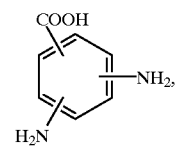
(XI)

or ammonia.

$R^6$ and $R^7$ of the formula III as $C_1$–$C_{12}$alkyl have the same meaning as $R^1$, $R^2$, $R^3$, $R^4$ and $R^5$ as $C_1$–$C_{12}$alkyl in the compounds of the formulae I and II.

Alkylamines or dialkylamines containing not more than 20 C atoms are, for example, methylamine, ethylamine, n-propylamine, isopropylamine, n-butylamine, isobutylamins, tert-butylamine, n-pentylamine, 2-pentylamine, 3-pentylamine, pentaerythrylamine and so on, or dimethylamine, diethylamine, di-n-propylamine, diisopropylamine, di-n-butylamine, diisobutylamin, di-tert-butylamine, di-n-pentylamine, di-2-pentylamine, di-3-pentylamine, dipentaerythrylamine and so on, i.e. amines whose C atom chains can be linear and branched. It is also possible to employ dialkylamines containing different alkyl chains, both linear and branched, such as methylisopropylamine for example. The polyamines of the formula IV comprise polyamines such as methylenediamine, 1,4-butylenediamine, 2-methylpentamethylenediamine, hexamethylenediamine (HMD), trimethylhexamethylenediamine (TMD), bishexamethylenetriamine (BHMD) or ethylenediamine (EDA), diethylenetriamine (DETA), triethylenetetramine (TETA), tetraethylenepentamine (TEPA), pentaethylenehexamine and so on, or 1,3-propylenediamine, 1,2-propylenediamine, dipropylenetriamine, tripropylenetetramine and so on, and also amines whose alkylene chains are branched, such as in diisopropylenetriamine. The terminal nitrogen atoms may also carry an alkyl substituent from the group consisting of methyl, ethyl, n-propyl and isopropyl. It is likewise possible to employ polyamines which contain cyclic rings. These rings can be either aromatic or cycloaliphatic.

Examples of typical monocyclic aromatic diamines are the xylylenediamines, for example m-xylylenediamine (MXDA).

Typical representatives of the cycloaliphatic diamines of the formula V are 1,2-diaminocyclohexane (1,2-DACH) or its isomers, or 1-methyl-2,4-diaminocyclohexane.

Isophoronediamine (IPD), 1,3-bisaminomethylcyclohexane (1,3-BAC) and

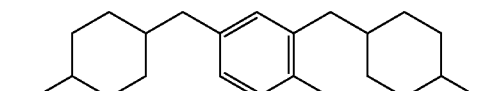

or

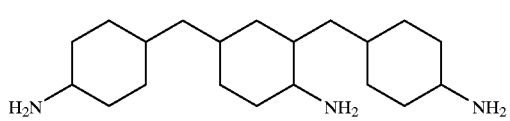

are further cycloalphatic polyamines which can be employed.

Examples of polyamines of the formula VI are:

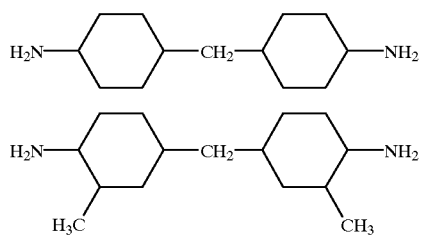

Norbornanediamine and N-2-aminoethylpiperazine are further typical representatives of polyamines.

Polyaminoamides of the formula VII contain up to 30 repeating amido units, it being possible for the carbon chain to be branched. Polyaminoamides may likewise be the reaction product of a saturated or unsaturated fatty acid and a polyamine, or, for example, the product of adipic acid and diethylenetriamine, i.e. the reaction product of a dicarboxylic acid and a polyamine.

The polyoxyalkylenepolyamines of the formula VIII which are suitable for the purposes of the present invention include, for example the Jeffamines® of Texaco Chemical Corporation [Texaco brochure, Publication No. SC-024, 102-0548].

Examples of aromatic amines of the formula IX are 4,4'-diaminodiphenylmethane (4,4'-DDM), 4,4'-diaminodiphenyl sulfone (4,4'-DDS), 4,4'-diaminodiphenyl ether, 3,3'-dimethyl-4,4'-diaminodiphenylmethane, 3,3'-diethyl-4,4'-diaminodiphenylmethane and so on.

Aminocarboxylic acids can be either aliphatic, cycloaliphatic or aromatic in nature; it is also possible for all three structural types to occur in one molecule. The aliphatic structures can be either straight-chain or branched. Heteroatoms can also be included.

One example of an aromatic aminocarboxylic acid is 3,5-diaminobenzoic acid, for example.

The invention also provides compounds obtainable by reacting compounds of the formula I with a carboxylic acid.

The acids in question here can be saturated or unsaturated, aliphatic or cycloaliphatic, aromatic or mixed aliphatic-aromatic acids, the number of rings possibly being even greater than two. The carboxylic acids may likewise be polybasic acids. Examples are the following acids:

formic acid, acetic acid, hydroxyacetic acid, aminoacetic acid, chloroacetic acid, trichloroacetic acid, thiolacetic acid, propionic acid, 2,2-dimethylpropanoic acid, 3-chloropropionic acid, thiolactic acid, 3-thiolpropionic acid, 3-chloro-2,2-dimethylpropanoic acid, butyric acid, isobutanoic acid, 2-methylbutanoic acid, 2-ethylbutanoic acid, valeric acid, 2-methylpentanoic acid, 2,2-dimethylpentanoic acid, 2-ethylhexanoic acid, 4-oxopentanoic acid, 6-aminohexanoic acid, 2-bromohexanoic acid, isooctanoic acid, isononanoic acid, isodecanoic acid, undecanoic acid, stearic acid, 12-hydroxystearic acid, 9-decenoic acid, oleic acid, undec-10-enecarboxylic acid, 12-hydroxyoctadec-9-enoic acid, 2-oxocyclopentanecarboxylic acid, cyclohexanecarboxylic acid, cyclohexanetricarboxylic acid, cyclohexylacetic acid, all-cis-1,2,3,4-cyclopentanetetracarboxylic acid, 2-cyclopentenylacetic acid, trimesic acid, benzoic acid, o-hydroxybenzoic acid, p-hydroxybenzoic acid, o-aminobenzoic acid, p-aminobenzoic acid, o-nitrobenzoic acid, m-nitrobenzoic acid, o-chlorobenzoic acid, p-chlorobenzoic acid, 2,4-dichlorobenzoic acid, acetylsalicylic acid, phenylacetic acid, 2-hydroxyphenylacetic acid, oxalic acid, methylsuccinic acid, hydroxysuccinic acid, chlorosuccinic acid, bromosuccinic acid, meso-2,3-dibromosuccinic acid, mercaptosuccinic acid, 2-oxoglutaric acid, azelaic acid, decanedicarboxylic acid, citric acid, methacrylic acid, dimethylacrylic acid, fumaric acid, maleic acid, methylmaleic acid, tartaric acid, phthalic acid, isophthalic acid, hexachloronorbornenedicarboxylic acid and so on.

Preference is given to citric acid, undecanoic acid, cyclohexanetricarboxylic acid and trimesic acid.

The invention additionally provides compounds obtainable by reacting compounds of the formula I with a dicarboxylic anhydride.

The anhydrides in question can be saturated or unsaturated, aliphatic or cycloaliphatic, aromatic or mixed aliphatic-aromatic anhydrides, it being possible for the number of rings to be even greater than two. Possible examples are the following dicarboxylic anhydrides:

acetic anhydride, propionic anhydride, maleic anhydride, methylmaleic anhydride, dodec-2-enylmaleic anhydride, 2-nonen-1-ylsuccinic anhydride, 2-dodecen-1-ylsuccinic anhydride, O,O'-diacetyltartaric anhydride, 1,2-cyclohexanedicarboxylic anhydride, 4-methyl-cis-1,2-cyclohexanedicarboxylic anhydride, tetrahydrophthalic anhydride, phthalic anhydride, 4-chlorophthalic anhydride, 4,5-dichlorophthalic anhydride, tetrachlorophthalic anhydride, trimellitic anhydride, norbornenedicarboxylic anhydride, hexachloronorbornenedicarboxylic anhydride, all-cis-1,2:3,4-cyclopentanetetracarboxylic anhydride, 1,2:4,5-benzenetetracarboxylic dianhydride and so on.

Preference is given to 1,2-cyclohexanedicarboxylic anhydride, phthalic anhydride and trimellitic anhydride.

The invention additionally provides compounds obtainable by reacting compounds of the formula I with a phenol. Examples of the phenols in question are:

o-tert-butylphenol, p-nonylphenol, p-dodecenylphenol, o-phenylphenol, p-phenylphenol, 4-chloro-2-methylphenol, 4-chloro-3-methylphenol, o-aminophenol, p-aminophenol, o-nitrophenol, p-nitrophenol, 2,4,6-trinitrophenol, o-chlorophenol, p-chlorophenol, 2,4,6-trichlorophenol, tetrachlorophenol, pentachlorophenol, 1-naphthol, 2-naphthol, o-hydroxybenzaldehyde, pyrocatechol, resorcinol, hydroquinone, bisphenol-A and so on. Preference is given to resorcinol and bisphenol A.

The invention also provides compounds obtainable by reacting compounds of the formula I with a metal alcoholate. Examples of preferred metal alcoholates are sodium methanolate, sodium ethanolate, potassium methanolate, potassium ethanolate, sodium isopropanolate or potassium tert-butanolate. Particular preference is given to sodium ethanolate or potassium tert-butanolate.

For all compounds mentioned it is the case that all possible isomers can be employed.

The invention provides, furthermore, compounds of the formula I which are adsorbed on a filler. The filler can be, for example, $TiO_2$, $SiO_2$, $CaCO_3$, $CaSO_4$, $BaSO_4$, $Al(OH)_3$, talc, carbon black, glass fibres or glass beads, cellulose or wood flour.

The epoxides of the formula I can be prepared in accordance with one of the methods described in EP-A-0 634 399, EP-A-0 001 835 or in Luston and Vass, Makromolekulare Chemie, Macromol. Symp. 27, 231 (1989).

Excess epichlorohydrin is judiciously added slowly to a piperidine compound of the formula Y

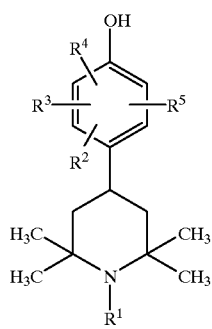

(Y)

in the presence of strong bases, for example concentrated aqueous alkali metal hydroxide solution, and in the presence or absence of an organic solvent. The base is advantageously employed in a from 2- to 20-fold molar excess relative to the starting compound; for example, from 3 to 15 mol, preferably from 4 to 12 mol, of sodium or potassium hydroxide are used as a 50% aqueous solution per mole of piperidine compound. The amount of organic solvent is judiciously such that the epoxide compound is fully dissolved. The reaction takes place judiciously in an inert solvent. Solvents which can be employed are polar or apolar organic solvents, for example hydrocarbons, ethers, ketones, amides, nitriles, tertiary amines, halogenated hydrocarbons or sulfoxides; suitable examples are toluene, hexane, cyclohexane, ligroin, petroleum ether and other hydrocarbon mixtures, dimethylformamide, methylene chloride, tetrahydrofuran, dioxane, diethyl ether, dimethyl sulfoxide and acetonitrile; particular preference is given to methylene chloride and toluene. To one equivalent of the piperidine starting compound it is possible to employ, for example, from 1 to 4, preferably from 1.2 to 3, and, in particular, from 1.5 to 2.5 equivalents of epichlorohydrin. Furthermore it is possible to add to the mixture advantageously from 0.01 to 10 mol-%, preferably from 2 to 4 mol %, of a tertiary amine salt, for example a tetraalkylammonium halide, such as tetramethylammonium chloride or tetrabutylammonium bromide, or of a phosphonium salt, for example a quaternary phosphonium halide, such as ethyltriphenylphosphonium bromide, as catalyst.

During the reaction the temperature can be in the range from 0 to 120° C., the temperature is judiciously from 10 to 80° C., in particular from 20 to 70° C.

The starting compounds of the formula Y are prepared, for example, from commercially obtainable triacetoneamine, which is reacted with phenol in concentrated hydrochloric acid solution judiciously at elevated temperature (C.A. 90:54839 g). Reduction of the hydrochloride with hydrogen by means of a catalyst then gives the unsubstituted or substituted 4-(4-hydroxyphenyl)-2,2,6,6-tetramethylpiperidine (DE-A-2 258 86). In order to introduce a substituent on the piperidine nitrogen the hydroxyl group of the phenyl ring must be protected in a manner known per se, for example with the aid of trimethylsilyl group.

Homopolymers, copolymers and terpolymers of compounds of the formula I are prepared judiciously by anionic polymerization to give, in particular, polyethers of the formula II. These may be linear in composition, composed entirely of identical repeating units, or else may be modified.

The polymerization can be performed, for example, in accordance with one of the methods described by K. C. Frisch and S. L. Reegen (Frisch/Reegen: Ring-Opening Polymerization, Marcel Dekker, New York 1969). The polymerization is generally initiated by one of the customary anionic polymerization initiators. These include basic organometallic compounds, such as Grignard compounds, for example of the type Cl—Mg—$C_1$–$C_{12}$alkyl or Cl—Mg—$C_6$–$C_{12}$aryl, alkali metal alkyls, for example alkali metal $C_1$–$C_6$alkyls such as tert-butylpotassium, alkali metal alcoholates Me—OR', in which Me is, for example, Li, Na, K and R' is $C_1$–$C_6$alkyl, examples being sodium or potassium methanolate, sodium or potassium tert-butylate, lithium or sodium methanolate, and hydroxides or amides, for example NaOH, KOH, sodium amide, lithium amide. The initiator is judiciously added in an amount of 0.1–20 mol-%, preferably 1–10 mol-%, based on the amount of epoxide of the formula I.

A crown ether such as 18-crown-6 or 15-crown-5 can be added to the mixture, judiciously in an amount of 0.1–10 mol-%, preferably 1–5 mol-%, based on the amount of epoxide of the formula I.

The molecular weights can be controlled by the amount of initiator added.

The polymerization can be conducted without solvent; however, the use of a solvent is preferred. The reaction temperature is not critical; in general it is varied within the range from 10 to 200° C.

Any solvents present must be inert under the reaction conditions. Suitable solvents include aromatic and/or aliphatic hydrocarbons and ethers. Preference is given to high-boiling solvents, for example those whose boiling temperature under atmospheric pressure is in the range 80–150° C. Examples of solvents that can be used are benzene, toluene, xylene, ethylbenzene, isopropylbenzene, cyclohexane, diethyl ether, dibutyl ether, tetrahydrofuran or dioxane.

The polymerization is expediently carried out with exclusion of oxygen, for example under argon or under nitrogen, and with exclusion of water.

After polymerization is complete the product can be worked up by customary methods; the mixture is, judiciously, diluted first of all with an appropriate solvent, for example tetrahydrofuran. The solution can be purified by filtration, directly or after dispersion of active charcoal. The polymer can be precipitated from the solution with the aid of a further solvent of appropriate polarity, for example acetonitrile; this can be done by introducing the polymer solution into a relatively large amount of the precipitant. If required, purification by precipitation can be repeated two or more times.

The chosen polymerization and workup conditions determine what end groups the polyethers of the formula II according to the invention will have. The terminal carbon atoms of the polyether chain can be satisfied, for example, by —H or —OH or by a radical of the compound used as initiator. If the initiator employed, for example, is one of the above-described alcoholates R'O⁻, and workup following polymerization is conducted with a protic solvent, it is often case that the end groups —OR' and —OH may occur on the terminal carbon atoms.

In principle, however, the nature of the end group is of minor importance for the effect of the novel polyether as stabilizer.

The preparation of the amino adducts according to the invention takes place in one reaction judiciously without solvent and at elevated temperature. The temperature during the reaction can be in the range from 80 to 250° C., expediently it is from 100 to 200° C., in particular from 170 to 190° C. For compounds where $R^1$=O—$C_1$–$C_{12}$alkyl, O—$C_5$–$C_8$cycloalkyl or O—CO—$C_1$–$C_{12}$alkyl, the reaction temperature is below 100° C.

Where compounds of the formula I are reacted with primary or secondary amines containing more than one reactive nitrogen, all or some or just one of the amino functions may react with the piperidine containing an epoxide function. It is likewise possible to employ for the reaction mixtures of two or more amines, which can react in the above way.

The reaction of the compounds of the formula I according to the invention with carboxylic acids, dicarboxylic anhydrides and also phenols takes place judiciously in a manner similar to that described in EP-A-0 634 399.

The reaction of the compounds of the formula I according to the invention with alkali metal alcoholates is carried out judiciously with sodium ethanolate or potassium tert-butanolate. Depending on the molar ratio between alcoholate and glycidyl ether the resulting products can range from 1:1 adducts to polymers.

The adsorption of the compounds of the formula I according to the invention onto at least one filler takes place judiciously in solution by impregnating the filler and then evaporating the solvent. If the reactions are performed in an inert solvent, the temperature of the reaction mixture can be held within the boiling range for the duration of the reaction (reflux). For this purpose a solvent-containing reaction mixture is heated to the boiling point, in general under atmospheric pressure, and the evaporated solvent is condensed with the aid of an appropriate condenser and returned to the reaction mixture.

The reaction can be carried out with the exclusion of oxygen, for example by flushing with an inert gas such as argon; however, in no case is oxygen a disruption, and so the reaction can also be carried out without taking this measure.

After the end of the reaction the reaction mixture can be worked up by customary methods; the mixture is judiciously diluted first of all with water, for example by adding the reaction mixture to 1–4 times the volume of (ice-)water; subsequently, the product can be separated off directly or subjected to extraction, examples of suitable extractants are ethyl acetate or toluene. If extraction is carried out, then the product can be isolated in a customary manner by removing the solvent; this takes place judiciously after the organic phase has been dried. Also possible is the insertion of further purification steps, for example washing with aqueous sodium bicarbonate solution, dispersing of active charcoal, chromatographing by means of silica gel, filtering, recrystallizing and/or distilling.

In the case of the reaction of the compounds of the formula I with primary or secondary amines or ammonia or with a carboxylic acid, a dicarboxylic anhydride, a phenol or alkali metal alcoholate, the principal products are compounds comprising the following structural elements A and/or B:

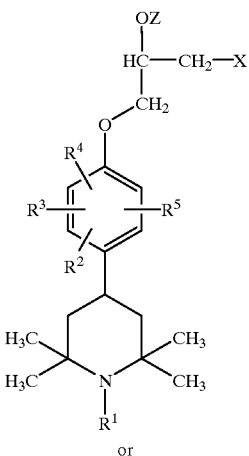
(A)

or

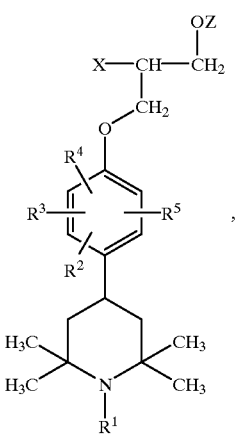
(B)

where Z is hydrogen or an alkali metal and X is the symbol for that nucleophilic radical of the amine or of the carboxylic acid or of the phenol or of the dicarboxylic anhydride or of the alcoholate that remains after Z has been removed, and $R^1$, $R^2$, $R^3$, $R^4$ and $R^5$ are as defined under formula I. In this context, the compounds of the formula A are formed preferentially and thus constitute the principal product.

The compounds of the formula I and also their novel homo-, co- and terpolymers and the compounds obtainable by reacting one or more compounds of the formula I with at least one further monoglycidyl compound, not of the formula I, and compounds obtainable by reacting one or more compounds of the formula I with at least one amine or with a carboxylic acid or with a phenol or dicarboxylic anhydride or alcoholate, and also compounds of the formula I which are adsorbed on a filler, are particularly suitable for stabilizing organic materials against thermal, oxidative and actinic breakdown.

Examples of such materials are:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), (VLDPE) and (ULDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (AA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly(α-methylstyrene).

6. Copolymers of styrene or α-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

7. Graft copolymers of styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfo-chlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride-vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/ butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides, polyetherimids, polyesterimids, polyhydantoins and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, isocyanates, isocyanurates, polyisocyanates or epoxy resins.

26. Crosslinked epoxy resins derived from aliphatic, cycloaliphatic, heterocyclic or aromatic glycidyl compounds, e.g. products of diglycidyl ethers of bisphenol A and bisphenol F, which are crosslinked with customary hardeners such as anhydrides or amines, with or without accelerators.

27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.

The invention therefore also provides compositions comprising a) an organic material which is sensitive to oxidative, thermal and/or actinic breakdown/buildup and b) at least one compound of the formula I, and the homo-, co- and terpolymers thereof according to the invention, and the compounds obtainable by reacting one or more compounds of the formula I with at least one further monoglycidyl compound, not of the formula I, and compounds obtainable by reacting one or more compounds of the formula I with at least one amine or with a carboxylic acid or with a phenol or dicarboxylic anhydride or alcoholate, and compounds of the formula I which are adsorbed on a filler, and provides for the use of compounds of the formula I and the homo-, co- and terpolymers thereof according to the invention and the compounds obtainable by reacting one or more compounds of the formula I with at least one further monoglycidyl compound, not of the formula I, and compounds obtainable by reacting one or more compounds of the formula I with at least one amine or with a carboxylic acid or with a phenol or dicarboxylic anhydride or alcoholate and compounds of the formula I which are adsorbed on a filler for stabilizing organic material against oxidative, thermal or actinic breakdown/buildup. The invention likewise embraces a method of stabilizing organic material against thermal, oxidative and/or actinic breakdown/buildup, which comprises adding to said material at least one compound of the formula I, and the homo-, co- and terpolymers thereof according to the invention, and the compounds obtainable by reacting one or more compounds of the formula I with at least one further monoglycidyl compound, not of the formula I, and compounds obtainable by reacting one or more compounds of the formula I with at least one amine or with a carboxylic acid or with a phenol or dicarboxylic anhydride or alcoholate, and compounds of the formula I which are adsorbed on a filler.

Of particular interest is the use of compounds of the formula I as stabilizers in synthetic organic polymers, and corresponding compositions.

The organic materials to be protected are preferably natural, semisynthetic or, preferably, synthetic organic materials. Particular preference is given to synthetic organic polymers or mixtures of such polymers, especially thermoplastic polymers such as polyolefins, in particular polyethylene (PE) and polypropylene (PP). Likewise particularly preferred organic materials are coating compositions. Coating compositions which are to be stabilized advantageously for the purposes of the invention are, for example, described in Ullmann's Encyclopedia of Industrial Chemistry, 5th ed., Vol. A18, pp. 359–464, VCH Verlagsgesellschaft, Weinheim 1991.

Of particular interest is the use of the compounds of the formula I according to the invention and the homo-, co- and terpolymers thereof according to the invention and the compounds obtainable by reacting one or more compounds of the formula I with at least one further monoglycidyl compound, not of the formula I, and compounds obtainable by reacting one or more compounds of the formula I with at least one amine or with a carboxylic acid or with a phenol or dicarboxylic anhydride or alcoholate, and compounds of the formula I which are adsorbed on a filler, as stabilizers for coatings, for example for paints. The invention therefore also provides those compositions whose component A is a film-forming binder.

The coating composition according to the invention contains preferably 0.01–10 parts by weight, in particular 0.05–10 parts by weight and especially 0.1–5 parts by weight of the stabilizer B according to the invention per 100 parts by weight of solid binder A.

Multicoat systems are also possible here, in which case the concentration of the compound of the formula I, and the homo-, co- and terpolymers thereof according to the invention, and the compounds obtainable by reacting one or more compounds of the formula I with at least one further monoglycidyl compound, not of the formula I, and compounds obtainable by reacting one or more compounds of the formula I with at least one amine or with a carboxylic acid or with a phenol or dicarboxylic anhydride or alcoholate, and compounds of the formula I which are adsorbed on a filler—(component B)—in the top layer can be higher, for example from 1 to 15 parts by weight, especially 3–10 parts by weight of B per 100 parts by weight of solid binder A.

The use of the compounds of the formula I, and the homo-, co- and terpolymers thereof according to the invention, and the compounds obtainable by reacting one or more compounds of the formula I with at least one further monoglycidyl compound, not of the formula I, and compounds obtainable by reacting one or more compounds of the formula I with at least one amine or with a carboxylic acid or with a phenol or dicarboxylic anhydride or alcoholate, and compounds of the formula I which are adsorbed on a filler, as stabilizer in coatings brings with it the additional advantage that delamination, i.e. the flaking of the coating from the substrate, is prevented. This advantage is particularly manifest in the case of metallic substrates, even in the case of multicoat systems on metallic substrates.

Suitable binders (component A) are in principle all those which are customary in the art, as are described in Ullmann's Encyclopedia of Industrial Chemistry, 5th ed., Vol. A 18, pages 368–426, VCH Verlagsgesellschaft, Weinheim 1991. The binder is generally a film-forming binder based on a thermoplastic or thermosetting resin, predominantly on a thermosetting resin. Examples thereof are alkyd, acrylic, polyester, phenolic, melamine, epoxy and polyurethane resins and mixtures thereof.

Component A can be a cold-curable or a heat-curable binder, the addition of a curing catalyst possibly being advantageous. Examples of suitable catalysts which accelerate the curing of the binder are described in Ullmann's Encyclopedia of Industrial Chemistry, Vol. A 18, p. 469, VCH Verlagsgesellschaft, Weinheim 1991.

Preference is given to coating compositions in which component A is a binder comprising functional acrylate resin and a crosslinker.

Examples of coating compositions with specific binders are:
1. paints based on cold- or heat-crosslinkable alkyd, acrylate, polyester, epoxy or melamine resins or mixtures of such resins, with or without addition of a curing catalyst;
2. two-component polyurethane paints based on hydroxyl-containing acrylate, polyester or polyether resins and on aliphatic or aromatic isocyanates, isocyanurates or polyisocyanates;
3. one-component polyurethane paints based on blocked isocyanates, isocyanurates or polyisocyanates, which are unblocked in the course of stoving;
4. one-component polyurethane paints based on aliphatic or aromatic urethanes or polyurethanes and on hydroxyl-containing acrylate, polyester or polyether resins;
5. one-component polyurethane paints based on aliphatic or aromatic urethanes or polyurethanes having free amine groups in the urethane structure and on melamine resins or polyether resins, with or without addition of a curing catalyst;
6. two-component paints based on (poly)ketimines and on aliphatic or aromatic diisocyanates, isocyanurates or polyisocyanates;
7. two-component paints based on (poly)ketimines and on an unsaturated acrylate resin or a polyacetoacetate resin or a methacrylamidoglycolate methyl ester;
8. two-component paints based on carboxyl- or amino-containing polyacrylates and polyepoxides;
9. two-component paints based on acrylate resins containing anhydride groups and on a polyhydroxy or polyamino component;
10. two-component paints based on acrylate-containing anhydrides and polyepoxides;
11. two-component paints based on (poly)oxazolines and on acrylate resins containing anhydride groups or unsaturated acrylate resins or aliphatic or aromatic isocyanates, isocyanurates or polyisocyanates;
12. two-component paints based on unsaturated polyacrylates and polymalonates;
13. thermoplastic polyacrylate paints based on thermoplastic acrylate resins or externally crosslinking acrylate resins in combination with etherified melamine resins;
14. paint systems based on siloxane-modified or fluorine-modified acrylate resins.

In addition to components A and B the coating composition may include further components, examples being solvents, pigments, dyes, plasticizers, stabilizers, thixotropic agents, drying catalysts and/or levelling assistants. Examples of possible components are those as described in Ullmann's Encyclopedia of Industrial Chemistry, 5th ed., Vol. A 18, pages 429–471, VCH Verlagsgesellschaft, Weinheim 1991.

Possible drying catalysts or curing catalysts are, for example, organometallic compounds, amines, amino-containing resins and/or phosphines. Examples of organometallic compounds are metal carboxylates, especially those of the metals Pb, Mn, Co, Zn, Zr or Cu, or metal chelates, especially those of the metals Al, Ti or Zr or organometallic compounds such as organotin compounds, for example.

Examples of metal carboxylates are the stearates of Pb, Mn or Zn, the octoates of Co, Zn or Cu, the naphthenates of Mn and Co or the corresponding linoleates, resinates or tallates.

Examples of metal chelates are the aluminium, titanium or zirconium chelates of acetylacetone, ethyl acetylacetate, salicylaldehyde, salicylaldoxime, o-hydroxyacetophenone or ethyl trifluoroacetylacetate, and the alkoxides of these metals.

Examples of organotin compounds are dibutyltin oxide, dibutyltin dilaurate and dibutyltin dioctoate.

Examples of amines are, in particular, tertiary amines, for example tributylamine, triethanolamine, N-methyldiethanolamine, N-dimethylethanolamine, N-ethylmorpholine, N-methylmorpholine or diazabicyclooctane(triethylenediamine) and the salts thereof. Further examples are quaternary ammonium salts, for example trimethylbenzylammonium chloride.

Amino-containing resins are simultaneously binder and curing catalyst. An example thereof are amino-containing acrylate copolymers.

Phosphines, for example triphenylphosphine, can also be used as curing catalyst.

The coating compositions according to the invention can also be radiation-curable coating compositions. In this case the binder consists essentially of monomeric or oligomeric compounds having ethylenically unsaturated bonds (prepolymers), which after application are cured, i.e. converted into a crosslinked, high molecular mass form, by actinic radiation. Where the system is a UV-curing system, it generally also includes a photoinitiator. Appropriate systems are described in the abovementioned publication, Ullmann's Encyclopedia of Industrial Chemistry, 5th ed., Vol. A 18, pages 451–453.

The coating compositions according to the invention can be applied to any desired substrates, for example to metal, wood, plastic or ceramic materials. In the case of the finishing of automobiles they are preferably used as topcoat. If the topcoat consists of two layers of which the lower layer is pigmented and the upper layer is not pigmented, then the coating composition according to the invention can be used for the upper or the lower layer or for both layers, but preferably for the upper layer.

The coating compositions according to the invention can be applied to the substrates by the customary techniques, for example by spreading, spraying, flowcoating, dipping or electrophoresis; see also Ullmann's Encyclopedia of Industrial Chemistry, 5th ed., Vol. A 18, pages 491–500.

Depending on the binder system the coatings can be cured at room temperature or by heating. The coatings are preferably cured at 50–150° C., powder coatings also at higher temperatures.

The coatings obtained in accordance with the invention have outstanding resistance to damaging effects of light, oxygen and heat; particular mention should be made of the good light stability and weather resistance of the resulting coatings, for example paints.

The invention therefore also provides a coating, especially a paint, which has been stabilized against damaging effects of light, oxygen and heat by adding a compound of the formula I, and the homo-, co- and terpolymers thereof according to the invention, and the compounds obtainable by reacting one or more compounds of the formula I with at least one further monoglycidyl compound, not of the formula I, and compounds obtainable by reacting one or more compounds of the formula I with at least one amine or with a carboxylic acid or with a phenol or dicarboxylic anhydride or alcoholate, and compounds of the formula I which are adsorbed on a filler. The paint is preferably a topcoat for automobiles. The invention also comprises a method of stabilizing a coating based on organic polymers against damage by light, oxygen and/or heat, which comprises admixing to said coating composition a compound of the formula I and the homo-, co- and terpolymers thereof according to the invention, and the compounds obtainable by reacting one or more compounds of the formula I with at least one further monoglycidyl compound, not of the formula I, and compounds obtainable by reacting one or more compounds of the formula I with at least one amine or with a carboxylic acid or with a phenol or dicarboxylic anhydride or alcoholate, and compounds of the formula I which are adsorbed on a filler, and the use of compounds of the formula I, and the homo-, co- and terpolymers thereof according to the invention, and the compounds obtainable by reacting one or more compounds of the formula I with at least one further monoglycidyl compound, not of the formula I, and compounds obtainable by reacting one or more compounds of the formula I with at least one amine or with a carboxylic acid or with a phenol or dicarboxylic anhydride or alcoholate, and compounds of the formula I which are adsorbed on a filler, in coating compositions as stabilizers against damage by light, oxygen and/or heat.

The coating composition may include an organic solvent or solvent mixture in which the binder is soluble. Alternatively, the coating composition can be an aqueous solution or dispersion. The vehicle can also be a mixture of an organic solvent and water. The coating composition can also be a high-solids coating material or can be solvent-free (for example a powder coating). Examples of power coatings are those described in Ullmann's Encyclopedia of Industrial Chemistry, 5th ed., A 18, pages 438–444. The powder coating may also be in the form of a powder slurry, i.e. a dispersion of the powder in—preferably—water.

The pigments can be inorganic, organic or metallic pigments. The coating compositions according to the invention preferably include no pigments and are used as transparent coating material.

Likewise preferred is the use of the coating composition as a topcoat for applications in the automotive industry, especially as a pigmented or nonpigmented topcoat of the paint system. Its use for underlying coats, however, is also possible.

Further materials to be stabilized with the compounds according to the invention are photographic materials. By such materials are meant in particular those described in Research Disclosure 1990, 31429 (pages 474–480) for photographic reproduction and other reprographic techniques.

In general the compounds of the formula I are added in amounts of from 0.01 to 10%, preferably from 0.01 to 5% and, in particular, from 0.01 to 2%, based on the overall weight of the stabilized composition, to the material that is to be stabilized. Particular preference is given to the use of the compounds according to the invention in amounts of from 0.05 to 1.5%, especially from 0.1 to 0.5%.

Incorporation into the materials can take place, for example, by mixing in or by applying the compounds of the formula I, with or without further additives, by the methods customary in the art. Where the materials are polymers, especially synthetic polymers, incorporation can take place before or during shaping, or by applying the dissolved or dispersed compound to the polymer, with or without subsequent evaporation of the solvent. In the case of elastomers these can also be stabilized as latices. A further option for incorporating the compounds of the formula I into polymers is to add them before, during or directly after the polymerization of the corresponding monomers and/or prior to crosslinking. In this case the compound of the formula I can be added as it is or else in encapsulated form (for example in waxes, oils or polymers). In the case of addition prior to or during polymerization the compounds of the formula I may also act as a regulator of the chain length of the polymers (chain terminator). The compounds of the formula I can also be added in the form of a masterbatch which contains these compounds in a concentration, for example, of from 2.5 to 25% by weight to the plastics that are to be stabilized.

The compounds of the formula I can judiciously be incorporated by the following methods:

as an emulsion or dispersion (for example to latices or emulsion polymers), as a dry mix during the mixing of additional components or polymer mixtures, by direct addition to the processing apparatus (for example extruders, internal mixers, etc.), as a solution or melt.

Polymer compositions according to the invention can be used in various forms or processed into various products, for example as (or to) films, fibres, tapes, moulding compounds, profiles, or as binders for coating materials, adhesives or putties.

In addition to the compounds of the formula I and the home-, co- and terpolymers and the compounds obtainable by reacting one or more compounds of the formula I with at least one further monoglycidyl compound, not of the formula I, and compounds obtainable by reacting one or more compounds of the formula I with at least one amine or with a carboxylic acid or with a phenol or dicarboxylic anhydride or alcoholate, and also compounds of the formula I which are adsorbed on a filler, the compositions according to the invention can as additional component (c) include one or more customary additives, for example the following:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1'-methylundec-1'-yl) phenol, 2,4-dimethyl-6-(1'-methylheptadec-1'-yl)phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxy-phenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl)adipate.

1.4. Tocopherols, for example α-tocopherol, β-tocopherol, γ-tocopherol, δ-tocopherol and mixtures thereof (Vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis(2,6-dimethyl-4-hydroxyphenyl)disulfide.

1.6. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl) butyrate], bis(3-tert-butyl-4-hydroxy-5-methylphenyl) dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis-(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra-(5-tert-butyl-4-hydroxy-2-methylphenyl)pentane.

1.7. O-, N- and S-benzyl compounds, for example 3,5,3',5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5-di-tert-butyl-4-hydroxybenzylmercaptoacetate.

1.8. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, didodecylmercaptoethyl-2,2-bis-(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl)malonate.

1.9. Aromatic hydroxybenzyl compounds, for example 1,3,5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine Compounds, for example 2,4-bis (octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris (3,5-di-tert-butyl-4-hydroxyphenoxy)-1,2,3-triazine, 1,3,5-tris-(3,5-di-tert-butyl-4-hydroxybenzyl)isocyanurate, 1,3,5-tris(4-tert-butyl-3-hydroxy-2,6-dimethylbenzyl) isocyanurate, 2,4,6-tris(3,5-di-tert-butyl-4-hydroxyphenylethyl)-1,3,5-triazine, 1,3,5-tris(3,5-di-tert-butyl-4 -hydroxyphenylpropionyl)-hexahydro-1,3,5-triazine, 1,3,5-tris(3,5-dicyclohexyl-4-hydroxybenzyl) isocyanurate.

1.11. Benzylphosphonates, for example dimethyl-2,5-di-tert-butyl-4-hydroxybenzylphosphonate, diethyl-3,5-di-tert-butyl-4-hydroxbenzylphosphonate, dioctadecyl3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl) propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl)isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methylphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15. Esters of β-(3,5-dicyclohexyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl) propionic acid e.g. N,N'-bis(3,5-di-tert-butyl-4-hydroxyphenylpropionyl)hexamethylenediamide, N,N'-bis (3,5-di-tert-butyl-4-hydroxyphenylpropionyl) trimethylenediamide, N,N'-bis(3,5-di-tert-butyl-4-hydroxyphenylpropionyl)hydrazide, N,N'-bis[2(3-[3,5-di-tert-butyl-4-hydroxyphenyl]propionyloxy)ethyl]oxamide (Naugard®XL-1 supplied by Uniroyal).

1.18. Ascorbic acid (vitamin C)

1.19. Aminic antioxidants, for example N,N'-di-isopropyl-p-phenylenediamine, N,N'-di-secbutyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenlenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl4dimethylaminomethylphenol, 2,4'-diaminodiphenylmethane, 4,4'-diaminodiphenylmethane, N,N, N',N'-tetramethyl-4,4'-diaminodiphenylmethane, 1,2-bis[(2-methylphenyl)amino]ethane, 1,2-bis(phenylamino) propane, (o-tolyl)biguanide, bis[4-(1',3'-dimethylbutyl) phenyl]amine, tert-octylated N-phenyl-1-naphthylamine, a mixture of mono- and dialkylated tert-butyl/tert-octyldiphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- und dialkylated tert-butyldiphenylamines, 2,3-dihydro-3,3-dimethyl-4H-1,4-benzothiazine, phenothiazine, a mixture of mono- und dialkylated tert-butyl/tert-octylphenothiazines, a mixture of mono- und dialkylated tert-octylphenothiazines, N-allylphenothiazin, N,N,N',N'-tetraphenyl-1,4-diaminobut-2-ene, N,N-bis-(2,2,6,6-tetramethylpiperid-4-yl-hexamethylenediamine, bis(2,2,6,6-tetramethylpiperid-4-yl)sebacate, 2,2,6,6-tetramethylpiperidin-4-one, 2,2,6,6-tetramethylpiperidin-4-ol.

2. UV Absorbers and Light Stabilisers 2.1. 2-(2'-Hydroxyphenyl)benzotriazoles, for example 2-(2'-hydroxy-5'-methylphenyl)-benzo-triazole, 2-(3',5'-di-tert-butyl-2'-hydroxyphenyl)benzotriazole, 2-(5'-tert-butyl-2'-hydroxyphenyl)benzotriazole, 2-(2'hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl) benzotriazole, 2-(2'-hydroxy-4'-octyloxyphenyl) benzotriazole, 2-(3',5'-di-tert-amyl-2'-hydroxyphenyl) benzotriazole, 2-(3',5'-bis-(α,α-dimethylbenzyl)-2'-hydroxyphenyl)benzotriazole, 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl) phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl) benzotriazole, 2-(3'-tert-butyl-5'-[2-(2-ethylhexyloxy) carbonylethyl]-2'-hydroxyphenyl)benzotriazole, 2-(3'-dodecyl-2'-hydroxy-5'-methylphenyl)benzotriazole, 2-(3'-tert-butyl-2'-hydroxy-5'-(2-isooctyloxycarbonylethyl) phenylbenzotriazole, 2,2'-methylene-bis-[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—CH$_2$CH$_2$—COO—CH$_2$CH$_2$-]$_2$ where R=3'-tert-butyl-4'-hydroxy-5'-2H-benzotriazol-2-ylphenyl, 2-[2'-hydroxy-3α-(α,α-dimethylbenzyl)-5'-(1,1,3,3-tetramethylbutyl) phenyl]benzotriazole; 2-[2'-hydroxy-3'-(1,1,3,3-tetramethylbutyl)-5'-(α,α-dimethylbenzyl)phenyl] benzotriazole.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutylphenyl salicylate, phenyl salicylate, octylphenyl salicylate, dibenzoyl resorcinol, bis (4-tert-butylbenzoyl)resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxy-cinnamate, butyl α-cyano-β-methyl-p-methoxy-cinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amines, for example bis(2,2,6,6-tetramethyl-4-piperidyl)sebacate, bis(2,2,6,6-tetramethyl-4-piperidyl)succinate, bis(1,2,2,6,6-pentamethyl-4-piperidyl) sebacate, bis(1-octyloxy-2,2,6,6-tetramethyl-4-piperidyl) sebacate, bis(1,2,2,6,6-pentamethyl-4-piperidyl)n-butyl-3, 5-di-tert-butyl-4-hydroxybenzylmalonate, the condensate of 1-(2-hydroxyethyl)-2,2,6,6-tetramethyl-4- hydroxypiperidine and succinic acid, linear or cyclic condensates of N,N'-bis(2,2,6,6-tetramethyl-4-piperidyl) hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl)-1,2,3,4-butane-tetracarboxylate, 1,1'-(1,2-ethanediyl)-bis-(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decan-2,4-dione, bis(1-octyloxy-2,2,6,6-tetramethylpiperidyl) sebacate, bis(1-octyloxy-2,2,6,6-tetramethylpiperidyl) succinate, linear or cyclic condensates of N,N'-bis-(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl) pyrrolidin-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, a condensation product of N,N'-bis(2,2,6,6-tetramethyl-4-piperidyl)hexamethylenediamine and 4-cyclohexylamino-2,6-dichloro-1,3,5-triazine, a condensation product of 1,2-bis(3-aminopropylamino)ethane and 2,4,6-trichloro-1,3,5-triazine as well as 4-butylamino-2,2,6,6-tetramethylpiperidine (CAS Reg. No. [136504-96-6]); N-(2,2,6,6-tetramethyl-4-piperidyl)-n-dodecylsuccinimid, N-(1,2,2,6,6-pentamethyl-4-piperidyl)-n-dodecylsuccinimid, 2-undecyl-7,7,9,9-tetramethyl-1-oxa-3,8-diaza-4-oxo-spiro[4,5]decane, a reaction product of 7,7,9,9-tetramethyl-2-cycloundecyl-1-oxa-3,8-diaza-4-oxospiro[4,5]decane und epichlorohydrin, 1,1-bis(1,2,2,6,6-pentamethyl-4-piperidyloxycarbonyl)-2-(4-methoxyphenyl)ethene, N,N'-bis-formyl-N,N'-bis(2,2,6,6-tetramethyl-4-piperidyl) hexamethylenediamine, diester of 4-methoxymethylene-malonic acid with 1,2,2,6,6-pentamethyl-4-hydroxypiperidine, poly[methylpropyl-3-oxy-4-(2,2,6,6-tetramethyl-4-piperidyl)]siloxane, reaction product of maleic acid anhydride-α-olefin-copolymer with 2,2,6,6-tetramethyl-4-aminopiperidine or 1,2,2,6,6-pentamethyl-4-aminopiperidine.

2.7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis-(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxy-propoxy) phenyl]-4,6-bis(2,4-dimethyl)-1,3,5 triazine, 2-[2-hydroxy-4-(2-hydroxy-3-octyloxy-propyloxy)phenyl]-4,6-bis(2,4-dimethyl)-1,3,5-triazine, 2-[4-(dodecyloxy/tridecyloxy-2-hydroxypropoxy)-2-hydroxy-phenyl]-4,6-bis(2,4-dimethylphenyl)-1,3,5-triazine, 2-[2-hydroxy-4-(2-hydroxy-3-dodecyloxy-propoxy)phenyl]-4,6-bis(2,4-dimethylphenyl)-1,3,5-triazine, 2-(2-hydroxy-4-hexyloxy) phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxy-propoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}4,6-bis(2,4-dimethylphenyl)-1,3,5-triazine.

3. Metal deactivators, for example N,N'-diphenyloxamide, N-salicylal-N'-salicyloyl hydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl) oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl)phosphite, trilauryl phosphite, trioctadecyl phosphite, distearyl pentaerythritol diphosphite, tris(2,4-di-tert-butylphenyl)phosphite, diisodecyl pentaerythritol diphosphite, bis(2,4-di-tert-butylphenyl) pentaerythritol diphosphite, bis(2,6-di-tert-butyl-4-methylphenyl)-pentaerythritol diphosphite, diisodecyloxypentaerythritol diphosphite, bis(2,4-di-tert-butyl-6-methylphenyl)pentaerythritol diphosphite, bis(2,4,6-tris(tert-butylphenyl)pentaerythritol diphosphite, tristearyl sorbitol triphosphite, tetrakis(2,4-di-tert-butylphenyl)4,4'-biphenylene diphosphonite, 6-isooctyloxy-2,4,8,10-tetra-tert-butyl-12H-dibenz[d,g]-1,3,2-dioxaphosphocin, 6-fluoro-2,4,8,10-tetra-tert-butyl-12-methyl-dibenz[d,g]-1,3,2-dioxaphosphocin, bis(2,4-di-tert-butyl-6-methylphenyl) methyl phosphite, bis(2,4-di-tert-butyl-6-methylphenyl) ethyl phosphite, 2,2',2"-nitrilo[triethyltris(3,3',5,5'-tetra-tert-butyl-1,1'-biphenyl-2,2'-diyl)phosphite], 2-ethylhexyl(3,3',5,5'-tetra-tert-butyl-1,1'-biphenyl-2,2'diyl)phosphite.

Especially preferred are the following phosphites:

Tris(2,4-di-tert-butylphenyl)phosphite (Irgafos®168, Ciba-Geigy), tris(nonylphenyl) phosphite, (A)

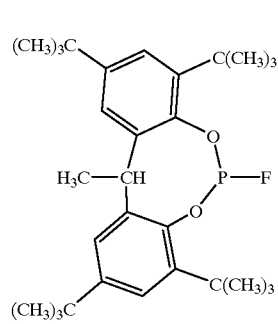

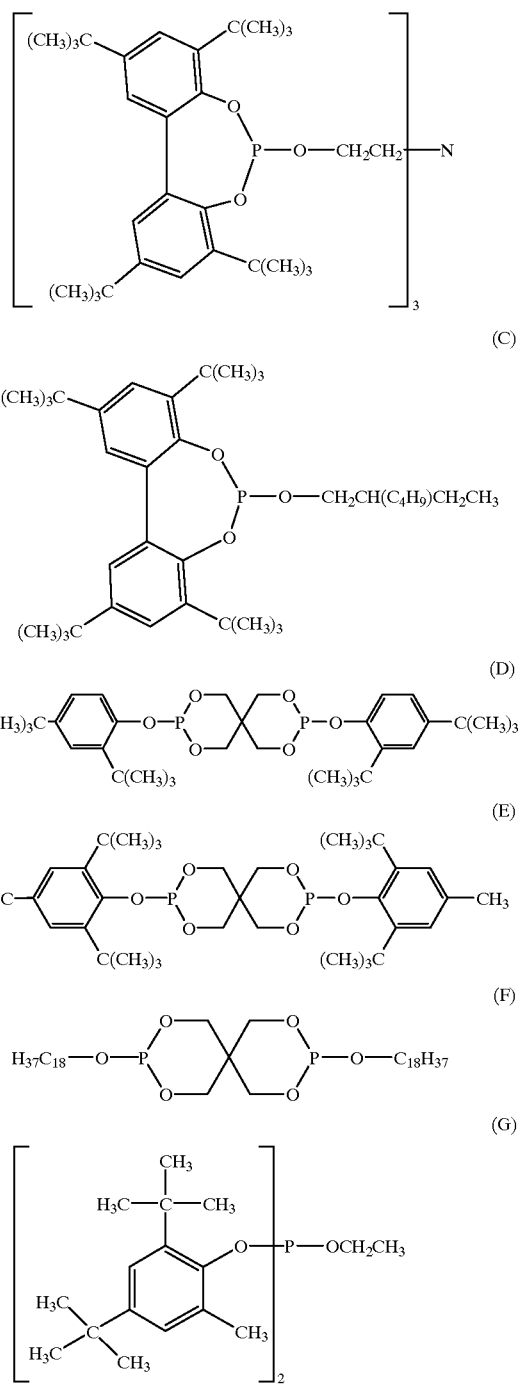

5. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

6. Nitrones, for example, N-benzyl-alpha-phenyl-nitrone, N-ethyl-alpha-methyl-nitrone, N-octyl-alpha-heptyl-nitrone, N-lauryl-alpha-undecyl-nitrone, N-tetradecyl-alpha-tridcyl-nitrone, N-hexadecyl-alpha-pentadecyl-nitrone, N-octadecyl-alpha-heptadecyl-nitrone, N-hexadecyl-alpha-heptadecyl-nitrone, N-ocatadecyl-alpha-pentadecyl-nitrone, N-heptadecyl-alpha-heptadecyl-nitrone, N-octadecyl-alpha-hexadecyl-nitrone, nitrone derived from N,N-dialkylhydroxylamine derived from hydrogenated tallow amine.

7. Thiosynergists, for example, dilauryl thiodipropionate or distearyl thiodipropionate.

8. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

9. Polyamide stabilisers, for example, copper salts in combination with iodides and/or phosphorus compounds and salts of divalent manganese.

10. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or zink pyrocatecholate.

11. Nucleating agents, for example, inorganic substances such as talcum, metal oxides such as titanium dioxide or magnesium oxide, phosphates, carbonates or sulfates of, preferably, alkaline earth metals; organic compounds such as mono- or polycarboxylic acids and the salts thereof, e.g. 4-tert-butylbenzoic acid, adipic acid, diphenylacetic acid, sodium succinate or sodium benzoate; polymeric compounds such as ionic copolymers (ionomers).

12. Fillers and reinforcing agents, for example, calcium carbonate, silicates, glass fibres, glass bulbs, asbestos, talc, kaolin, mica, barium sulfate, metal oxides and hydroxides, carbon black, graphite, wood flour and flours or fibers of other natural products, synthetic fibers.

13. Other additives, for example, plasticisers, lubricants, emulsifiers, pigments, rheology additives, catalysts, flow-control agents, optical brighteners, flameproofing agents, antistatic agents and blowing agents.

14. Benzofuranones and indolinones, for example those disclosed in U.S. Pat. No. 4,325,863; U.S. Pat. No. 4,338,244; U.S. Pat. No. 5,175,312; U.S. Pat. No. 5,216,052; U.S. Pat. No. 5,252,643; DE-A-4316611; DE-A-4316622; DE-A-4316876; EP-A-0589839 or EP-A-0591102 or 3-[4-(2-acetoxyethoxy)phenyl]-5,7-di-tert-butyl-benzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butyl-benzofuran-2-one, 3-(3,5-dimethyl-4-pivaloyloxyphenyl)-5,7-di-tert-butyl-benzofuran-2-one, 3-(3,4-dimethylphenyl)-5,7-di-tert-butyl-benzofuran-2-one, 3-(2,3-dimethylphenyl)-5,7-di-tert-butyl-benzofuran-2-one.

These additional additives are judiciously employed in amounts of 0.1–10, for example 0.2–5% by weight, based on the polymer to be stabilized.

The examples which follow illustrate the invention in more detail. All parts and percentages, in the examples, in the remainder of the description and in the patent claims, are by weight unless specified otherwise. The examples employ the following abbreviations:

CDCl$_3$: deuterochloroform
Da: daltons
GC: gas chromatography
$^1$H-NMR: nuclear magnetic resonance of the nuclide $^1$H
MALDI-MS: matrix assisted laser desorption/ionization—mass spectroscopy
M$_n$: number-average molar mass (units g/mol)
M$_w$: mass-average molar mass (units g/mol)
T$_g$: glass transition temperature
TGA: thermogravimetric analysis—10% weight loss at a defined temperature

PREPARATION EXAMPLES

B1) 4-[4-(2,3-Epoxypropoxy)phenyl]-2,2,6,6-tetramethylpiperidine

B1a) 4-(4-Hydroxyphenyl)-2,2,6,6-tetramethyl-cyclo-1-aza-hex-3-ene hydrochloride 77.6 g (0.5 mol) of triacetoneamine and 49.8 g (0.53 mol) of phenol are melted at 60° C. in a 750 ml sulfonating flask. 135 ml of concentrated hydrochloric acid are added dropwise over the course of 30 minutes. The yellow solution is stirred at 70° C. for 24 hours and then cooled to room temperature. The solid is separated off and washed with methylene chloride. The crystals are dried at 80° C. under a high vacuum.

Yield: 107 g (79%)

Microanalysis: N content 4.5% (theory 5.2%)

B1b) 4-(4-Hydroxyphenyl)-2,2,6,6-tetramethylpiperidine 107 g (0.4 mol) of the hydrochloride prepared in B1a) are dissolved in 1.2 liters of methanol, 13 g of 5% platinum/C catalyst are added, and the hydrochloride is reduced to hydrogen at atmospheric pressure. After 3 hours the theoretical amount of hydrogen (10 liters) has been taken up. The catalyst is separated off. The solvent is removed by distillation on a rotary evaporator. The residue is taken up in 400 ml of water and boiled. The fine suspension is poured into 138 g (1 mol) of potassium carbonate in solution in 150 ml of water. The suspension is then cooled to room temperature and the solid is separated off. The solid is washed thoroughly with water and dried at 80° C. under a high vacuum.

Yield: 75 g (80%)

Melting point: 211–213° C.

A sample recrystallized from xylene melts at 214° C.

B1c) 4-[4-(2,3-Epoxypropoxy)phenyl]-2,2,6,6-tetramethylpiperidine

A 1.5 liter sulfonating flask with KPG stirrer, internal thermometer and dropping funnel is charged with 135 g (580 mmol) of the substance prepared in analogy to B1b), 266 g (2.87 mol) of epichlorohydrin and 7.8 g (23 mmol) of tetrabutylammonium hydrogen sulfate. 270 g of sodium hydroxide in solution in 270 ml of water are added dropwise with stirring at a rate such that the internal temperature is less than or equal to 30° C. Following the dropwise addition of the sodium hydroxide solution vigorous stirring is continued for 3 hours. The mixture is diluted with 200 ml of toluene, the aqueous phase is separated off and the organic phase is washed with ice-water. The organic phase is then dried over sodium sulfate and consequently concentrated by evaporation. The residue is distilled over a short-path distillation apparatus.

Boiling point of the liquid: 135° C./0.07 torr

Yield: 59 g (35%)

Melting point: 40° C.

Microanalysis:

| | calculated | found |
|---|---|---|
| C | 74.70% | 74.16% |
| H | 9.40% | 9.73% |
| N | 4.84% | 5.03% |

$^1$H-NMR (CDCl$_3$):

| | | |
|---|---|---|
| 0.6–0.8 ppm | (1H, s) | NH |
| 1.14 ppm and 1.27 ppm | (12H, s) | CH$_3$ |
| 1.18–1.26 ppm | (2H, m) | CH$_2$ ax. (piperidine) |
| 1.71–1.76 ppm | (2H, m) | CH$_2$ eq. (piperidine) |
| 2.72–2.75 ppm and 2.87–2.90 ppm | (2H, m) | CH$_2$ (epoxide) |
| 2.92–3.01 ppm | (1H, m) | CH (piperidine) |
| 3.32–3.36 ppm | (1H, m) | CH (epoxide) |
| 3.91–3.96 ppm and 4.16–4.21 ppm | (2H, m) | —O—CH$_2$ epoxide |
| 6.85 ppm and 6.88 ppm 7.12 ppm and 7.15 ppm | (4H, d) | aromatic |

B2) 4-[4-(2,3-Epoxypropoxy)phenyl]-1,2,2,6,6-pentamethylpiperidine

B2a) 4-[4-Trimethylsilyloxy]phenyl-2,2,6,6-tetramethylpiperidine

In a 1.5 liter sulfonating flask with KPG stirrer, internal thermometer and dropping funnel, 70 g (0.3 mol) of the substance prepared in analogy to B1b) are dissolved under argon in 700 ml of toluene. 105 ml of triethylamine (0.75 mol) are added, and the mixture is heated to 80° C. Then 35.8 g (0.33 mol) of trimethylchlorosilane are added slowly dropwise, and the mixture is stirred at 80° C. for a further 20 hours. It is cooled, and insoluble hydrochloride salt is separated off. The solvent is removed by evaporation and the residue is distilled under a high vacuum, to give 38 g (42%) of a liquid whose boiling point is 120° C./0.01 torr.

Microanalysis:

| | calculated | found |
|---|---|---|
| C | 70.76% | 70.71% |
| H | 10.23% | 10.54% |
| N | 4.58% | 4.56% |
| Si | 9.19% | 9.20% |

B2b) 4-(4-Hydroxyphenyl)-1,2,2,6,6-pentamethylpiperidine

In a 250 ml round-bottomed flask 30.6 g (0.1 mol) of the substance prepared in B2a), 13.8 g (0.11 mol) of dimethyl sulfate and 17.9 g (0.13 mol) of potassium carbonate are dissolved under nitrogen in 150 ml of methyl ethyl ketone and the solution is boiled under reflux for 20 hours. First the solid is separated off and then the solvent is removed. The oil which remains is dissolved in 100 ml of acetic acid and precipitated in concentrated potassium carbonate solution. The precipitate is separated off and washed with water. The dry substance is recrystallized from n-hexane.

Yield: 20.2 g (82%)

Melting point: 145° C.

Microanalysis:

|   | calculated | found |
|---|---|---|
| C | 77.68% | 77.71% |
| H | 10.49% | 10.33% |
| N | 5.66% | 5.83% |

B2c) 4-[4-(2,3-Epoxypropoxy)phenyl]-1,2,2,6,6-pentamethylpiperidine

In a 250 ml round-bottomed flask, equipped with magnetic stirrer and condenser, 18.6 g (75 mmol) of the substance prepared in B2b) are stirred in 50 ml of epichlorohydrin at 70° C. for 4 hours. Then excess epichlorohydrin is removed and the yellow oil is emulsified in a little water and stirred with 30 ml of 50% strength sodium hydroxide solution at 70° C. Once cooled, the solution is subjected to extraction with methylene chloride. The organic phase is dried and then concentrated by evaporation. The residue is distilled in a bulb tube.

This gives 9.5 g (42%) of a pale yellow oil having a boiling point of 150° C./0.01 torr.

Microanalysis:

|   | calculated | found |
|---|---|---|
| C | 75.21% | 75.17% |
| H | 9.63% | 9.57% |
| N | 4.62% | 4.69% |

The following substances are prepared in analogy to the above preparation examples B1a), B1b) and B2a) and B2b)

TABLE 1

| Example | Structure | Melting point recrystallized from |
|---|---|---|
| B3 | (structure: 2,2,6,6-tetramethylpiperidine with N—H, 4-substituted with 3-methyl-4-hydroxyphenyl) | 170° C. toluene |
| B4 | (structure: 1,2,2,6,6-pentamethylpiperidine, 4-substituted with 3-methyl-4-hydroxyphenyl) | 130° C. n-hexane |
| B5 | (structure: 1,2,2,6,6-pentamethylpiperidine, 4-substituted with 3-isopropyl-4-hydroxyphenyl) | 132° C. n-hexane |
| B6 | (structure: 2,2,6,6-tetramethylpiperidine with N—H, 4-substituted with 3-tert-butyl-4-hydroxyphenyl) | 213° C. isopropanol |

TABLE 1-continued

| Example | Structure | Melting point recrystallized from |
|---|---|---|
| B7 | (structure: 2,2,6,6-tetramethylpiperidine attached to cyclohexyl-substituted hydroxyphenyl) | 215° C. isopropanol |
| B8 | (structure: 1-propargyl-2,2,6,6-tetramethylpiperidine attached to 4-hydroxyphenyl) | 151° C. toluene |

B9) 4-[4-(2,3-Epoxypropoxy)phenyl]-1-propargyl-2,2,6,6-tetramethylpiperidine A 750 ml sulfonating flask equipped with KPG stirrer and internal thermometer is charged with 64 g (236 mmol) of the compound B8, 87.3 g (943 mmol) of epichlorohydrin, 300 ml of 50% strength sodium hydroxide solution, 200 ml of methylene chloride and 3.2 g (9.4 mmol) of tetrabutylammonium hydrogen sulfate. This mixture is stirred vigorously at room temperature. After 4 hours the reaction mixture is filtered through a glass suction filter and the organic phase is separated off. Following evaporation of the solvents, the residue is dissolved while still hot in n-hexane and is recrystallized.

This gives 22 g (28%) of a solid which melts at 71° C.
Microanalysis:

|   | calculated | found |   |   |
|---|---|---|---|---|
| C | 77.02% | 76.95% |   |   |
| H | 8.93% | 8.97% |   |   |
| N | 4.28% | 4.37% |   |   |

$^1$H-NMR (CDCl$_3$):

| 1.13 ppm and 1.26 ppm | (12H, s) | CH$_3$ |
| 1.57–1.70 ppm | (4H, m) | CH$_2$ (piperidine) |
| 2.13–2.14 ppm | (1H, t) | C≡C—H |
| 2.73–2.76 ppm and 2.88–2.92 ppm | (2H, m) | CH$_2$ (epoxide ring) |
| 2.85–2.96 ppm | (1H, m) | Ar—CH< |
| 3.32–3.37 ppm | (1H, m) | CH (epoxide ring) |
| 3.36–3.37 ppm | (2H, d) | N—CH$_2$ |
| 3.91–3.97 ppm and 4.16–4.21 ppm | (2H, m) | O—CH$_2$— |
| 6.83–6.88 ppm and 7.12–7.17 ppm | (4H, m) | Ar—H |

B10) 4-[4-(2,3-Epoxypropoxy)-3-methylphenyl]-1,2,2,6,6-pentamethylpiperidine A 200 ml sulfonating flask with magnetic stirrer and thermometer is charged with 20 ml of epichlorohydrin, 50 ml of 50% strength sodium hydroxide solution and 0.23 g of tetrabutylammonium hydrogen sulfate. 4.5 g (17.2 mmol) of the substance B4 are added at room temperature to this emulsion. Conversion is complete after 6 hours. The organic phase is separated off, dried and concentrated by evaporation. The residue is distilled in a bulb tube. This gives 2.7 g (50%) of a clear liquid having a boiling point of about 200° C. at 0.01 torr.

Microanalysis:

|   | calculated | found |
|---|---|---|
| C | 75.67% | 75.52% |
| H | 9.84% | 9.91% |
| N | 4.41% | 4.45% |

$^1$H-NMR (CDCl$_3$):

| 1.09 und 1.16 ppm | (12H, s) | CH$_3$ (piperidine) |
| 1.55–1.67 ppm | (4H, m) | CH$_2$ (piperidine) |
| 2.23 ppm | (3H, s) | CH$_3$ (aromatic) |
| 2.29 ppm | (3H, s) | N—CH$_3$ |
| 2.75–2.90 ppm | (3H, m) | CH$_2$ (epoxide) and C—H (piperidine) |
| 3.32–3.37 ppm | (1H, m) | C—H (epoxide) |
| 3.92–3.98 ppm and 4.16–4.21 ppm | (2H, m) | O—CH$_2$ |
| 6.73–6.76 ppm | (1H, d) | C—H (aromatic) |
| 6.98–7.02 ppm | (2H, m) | C—H (aromatic) |

B10a) 4-[4-(2,3-Epoxypropoxy)-3-tert-butylphenyl]-2,2,6,6-tetramethylpiperidine Following the method of Example B10, 4.9 g (17 mmol) of the phenol B6 are reacted with 20 ml of epichlorohydrin. The crude product is distilled in a bulb tube. This gives 2 g (34%) of a colourless liquid which boils at 170° C./0.01 torr. The substance solidifies spontaneously and has a melting point of 88° C.

Microanalysis:

|   | calculated | found |
|---|---|---|
| C | 76.48% | 75.75% |
| H | 10.21% | 10.34% |
| N | 4.05% | 3.84% |

$^1$H-NMR (CDCl$_3$):

| 0.72 ppm | (1H, s) | NH |
|---|---|---|
| 1.15 ppm | (6H, s) | CH$_3$ (pipendine) |
| 1.19–1.23 ppm | (2H, m) | CH$_2$ (piperidine) |
| 1.28 ppm | (6H, s) | CH$_3$ (piperidine) |
| 1.41 ppm | (9H, s) | tert-butyl |
| 1.72–1.77 ppm | (2H, m) | CH$_2$ (piperidine) |
| 2.76–2.79 and 2.92–2.94 ppm | (2H, m) | O—CH$_2$— (epoxide ring) |
| 2.95–3.00 ppm | (1H, m) | C—H (piperidine) |
| 3.37–3.42 ppm | (1H, m) | CH—O (epoxide ring) |
| 3.96–4.02 and 4.20–4.25 ppm | (2H, m) | —CH$_2$—O— |
| 6.77–6.80 and 6.99–7.02 and 7.12–7.13 ppm | (3H, m) | C—H (aromatic) |

B11) Poly{4-[4-(2,3-Epoxypropoxy)-3-methylphenyl]-1,2,2,6,6-pentamethylpiperidine}

A 10 ml round-bottomed flask is charged with 2 g (6.3 mmol) of the substance prepared under B10, with 30 mg (0.3 mmol) of potassium tert-butylate and with 2 g of toluene, and this mixture is heated at 110° C. for 8 hours. GC analysis shows that there is no longer any monomer. The solvent is removed by evaporation and the residue is dried under a high vacuum.

This gives 2 g (100%) of a solid.

Microanalysis:

|   | calculated | found |
|---|---|---|
| C | 75.67% | 74.59% |
| H | 9.84% | 9.85% |
| N | 4.41% | 4.09% |

TGA (air, 2° C./min heating rate): 10% weight loss at 284° C.

MALDI-MS: $M_n$=4000, $M_w$=6100

B12) Poly{4-[4-(2,3-epoxypropoxy)phenyl]-2,2,6,6-tetramethylpiperidine}

A 250 ml round-bottomed flask equipped with magnetic stirrer and condenser is charged under argon gas with 37 g (128 mmol) of the compound prepared in Example B1c), with 0.3 g (2.7 mmol) of potassium tert-butanolate and with 80 ml of toluene. The mixture is reacted at reflux for 8 hours and then cooled to room temperature. The polymer is precipitated by introducing the reaction solution into 700 ml of acetonitrile. The polymer is subsequently dried at 100° C. under a high vacuum for 3 hours.

Yield: 33 g (89%)

Melting range maximum in the DSC: 63° C. (DSC, N$_2$, 10° C./min.)

Microanalysis:

|   | calculated | found |
|---|---|---|
| C | 74.70% | 73.75% |
| H | 9.40% | 9.18% |
| N | 4.84% | 4.91% |

TGA (air, 2° C/min.): 10% weight loss at 335° C.

MALDI-MS: Mn=3500, Mw=6000

B13) Terpolymer A

A 100 ml round-bottomed flask fitted with a magnetic stirrer, a reflux condenser and dropping funnel is charged under argon with 7 g (24 mmol) of the compound prepared in B1c) and 330 mg (2.9 mmol) of potassium tert-butylate in 10 ml of toluene. The reaction mixture is stirred at reflux for 5 hours. Analysis by gas chromatography indicates complete conversion of the compound B1c). 5.5 g (24 mmol) of 4-(2,3-epoxypropoxy)-1,2,2,6,6-pentamethylpiperidine and 5.2 g (24 mmol) of 4-(2,3-epoxypropoxy)-2,2,6,6-tetramethylpiperidine in 8 ml of toluene are added via a dropping funnel to the hot reaction solution, and the mixture is stirred under reflux for 17 hours more. GC indicates that there is no longer any monomer. The reaction solution is cooled and the toluene is removed completely be evaporation. This gives 18 g (100%) of a semisolid polymer having a glass transition point (T$_g$) of 21° C.

In the TGA (2° C./min., air) a 10% weight loss is found at 298° C.

MALDI-MS: $M_n$=2190, $M_w$=2930

B14) Terpolymer B

As described under B13), the same amounts of monomers, solvent and initiator are charged simultaneously to a vessel and polymerized. After 6 hours, GC indicates that there are no longer any monomers. Evaporation of the solvent gives 18 g (100%) of a polymer which has a glass transition point (T$_g$) of 21.5° C.

The TGA (2° C./min., air) shows a 10% weight loss at 302° C.

MALDI-MS: $M_n$=4800, $M_w$=6190

B15) Adduct of 4-[4-(2,3-epoxypropoxy)phenyl]-1-propargyl-2,2,6,6-tetramethylpiperidine and 4,4'-diaminodiphenyl sulfone A 100 ml round-bottomed flask with magnetic stirrer is charged under argon with 10.7 g (43 mmol) of 4,4'-diaminodiphenyl sulfone and 45.2 g (180 mmol) of the substance prepared in B9). The mixture is heated at 180° C. for 24 hours. Subsequently, excess 4-[4-(2,3-epoxypropoxy)phenyl]-1-propargyl-2,2,6,6-tetramethylpiperidine is separated from the reaction mixture under a high vacuum. The residue is cooled and pulverized.

Yield: 44.2 g (82%)

Melting point: 61° C.

Microanalysis:

|   | calculated | found |
|---|---|---|
| C | 68.97% | 67.91% |
| H | 9.00% | 8.83% |

-continued

|   | calculated | found |
|---|---|---|
| N | 6.70% | 6.44% |
| S | 2.56% | 2.52% |

TGA (air, 2° C./min. heating rate): 10% weight loss at 300° C.

MALDI-MS: Ion signal of greatest intensity at 1254.8 Da

EXAMPLE I

Light Stabilization of Polypropylene Fibres 2.5 g of the stabilizer according to the invention from Example B12) are mixed, together with 1 g of tris(2,4-di-tert-butylphenyl)phosphite, 1 g of calcium monoethyl 3,5-di-tertbutyl-4-hydroxybenzylphosphonate, 1 g of calcium stearate and 2.5 g of $TiO_2$ (Kronos RN 57), with 1000 g of polypropylene powder (melt index 12 g/10 min, measured at 230° C./2.16 kg) in a turbo mixer. The mixtures are extruded at 200–230° C. to granules; these granules are subsequently processed to fibres with the aid of a pilot plant (Leonard; Sumirago/VA, Italy) under the following conditions:

Extruder temperature: 190–230° C.
Head temperature: 255–260° C.
Draw ratio: 1:3.5
Drawing temperature: 120° C.
Fibres: 12 den The fibres produced in this way are exposed against a white background in a Weather-O-Meter® type 65 WR (Atlas Corp.) with a black standard temperature of 63° C. in accordance with ASTM D 2565-85. After different exposure times the residual tensile strength of the samples is measured. From the measurements a calculation is made of the exposure time $T_{50}$ after which the tensile strength of the samples is just half its original magnitude.

For comparison purposes, fibres without stabilizer according to the invention are produced and tested under otherwise identical conditions. The test results are compiled in Table 2.

TABLE 2

| Period of exposure until initial tensile strength is halved | |
|---|---|
| Stabilizer | Exposure period |
| none | 300 h |
| from Example 12 | 1640 h |

The fibres stabilized in accordance with the invention show an outstanding retention of strength.

EXAMPLE II

Stabilization of a Two-Coat Finish

The stabilizer according to the invention from Example B1c) is incorporated into 5–10 g xylene and tested in a clearcoat having the following composition:

| Synthacryl ® SC 303 [1] | 27.51 g |
|---|---|
| Synthacryl ® SC 370 [2] | 23.34 g |
| Maprenal ® MF 650 [3] | 27.29 g |
| Butyl acetate/butanol (37/8) | 4.33 g |
| Isobutanol | 4.87 g |
| Solvesso ® 150 [4] | 2.72 g |
| Crystal oil K-30 [5] | 8.74 g |
| Levelling assistant Baysil ® MA [6] | 1.20 g |
| | 100.00 g |

1) Acrylate resin from Hoechst AG; 65% solution in xylene/butanol 26:9
2) Acrylate resin from Hoechst AG; 75% solution in Solvesso® 100[4)]
3) Melamine resin from Hoechst AG; 55% solution in isobutanol
4) Manufacturer: ESSO
5) Manufacturer: Shell
6) 1% in Solvesso® 150; manufacturer: Bayer AG 1% of stabilizer from Example B1c) (in xylene), based on the solids content of the coating material, is added to the clearcoat. A clearcoat containing no light stabilizer is used as comparison.

The clearcoat is diluted to spray viscosity with Solvesso® 100 and is applied to a prepared aluminium panel (coil coat, filler, silver-metallic basecoat) and stoved at 130° C. for 30 minutes. The result is a dry film thickness of 40–50 mm of clearcoat.

The samples are then weathered in a UVCON® weathering apparatus from Atlas Corp. (UVB-313 lamps) with a cycle of 4 h of UV irradiation at 60° C. and 4 h of condensation at 50° C.

The samples are inspected at regular intervals for cracks.

The samples with the stabilizer according to the invention show high resistance to cracking.

EXAMPLE III

Stabilization of a Photographic Material 0.087 g of the yellow coupler of the formula is dissolved in 2.0 ml of a solution of the stablizer according to the invention from Example B1c) in ethyl acetate (2.25 g/100 ml). To 1.0 ml of this solution there are added 9.0 ml of a 2.3% strength aqueous gelatine solution adjusted to a pH of 6.5 and containing 1.744 g/l of the wetting agent of the formula

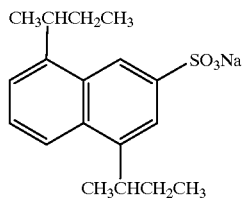

To 5.0 ml of the resulting coupler emulsion there are added 2 ml of a silver bromide emulsion having a silver content of 6.0 g/l and 1.0 ml of a 0.7% strength aqueous solution of the hardener of the formula

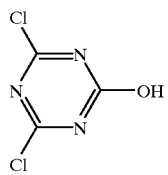

and the resulting composition is poured onto a piece of plastic-coated paper measuring 13×18 cm. After a curing time of 7 days the samples are exposed behind a silver step wedge to 125 lux.s and are then processed in the Kodak Ektaprint 2® process. =p The yellow wedges obtained are irradiated in an Atlas Weather-Ometer® with a 2500 W xenon lamp through a UV filter (Kodak 2C) with a total of 60 kJ/cm².

A sample without stabilizer goes through the same process, as a control.

The loss in colour density, at the absorption maximum of the yellow dye, which occurs in the course of irradiation is measured with a Macbeth densitometer TR 924 A.

The light stabilization effect is evident from the loss in colour density. The smaller the loss in density, the higher the light stabilizer activity.

The yellow wedges obtained are irradiated in an Atlas Weather-Ometer® with a 2500 W xenon lamp through a UV filter (Kodak 2C) with a total of 60 kJ/cm².

A sample without stabilizer goes through the same process, as a control.

The loss in colour density, at the absorption maximum of the yellow dye, which occurs in the course of irradiation is measured with a Macbeth densitometer TR 924 A.

The light stabilization effect is evident from the loss in colour density. The smaller the loss in density, the higher the light stabilizer activity.

The stabilizer according to the invention shows a good light stabilizing effect.

EXAMPLE IV
Stabilization of Polypropylene Tapes 1.0 g of the stabilizer according to the invention from Example B12) is mixed, together with 1 g of tris(2,4-di-tert-butylphenyl)phosphite, 0.5 g of pentaerythrityl tetrakis (3-[3',5'-di-tert-butyl-4'-hydroxyphenyl]propionate and 1 g of calcium stearate with 1000 g of polypropylene powder (STATOILMF; melt index 4.0 g/10 min, measured at 230° C./2.16 kg) in a turbo mixer.

The mixtures are extruded at 200–230° C. to granules; these granules are subsequently processed to 2.5 mm wide stretch tapes 50 μm thick with the aid of a pilot plant (Leonard; Sumirago/VA, Italy) under the following conditions:
Extruder temperature: 210–230° C.
Head temperature: 240–260° C.
Draw ratio: 1:6
Drawing temperature: 110° C.

The tapes produced in this way are exposed against a white background in a Weather-O-Meter® type 65 WR (Atlas Corp.) with a black standard temperature of 63° C. in accordance with ASTM D 2565-85. After different exposure times the residual tensile strength of the samples is measured. From the measurements a calculation is made of the exposure time $T_{50}$ after which the tensile strength of the samples is just half its original magnitude.

For comparison purposes, tapes without stabilizer according to the invention are produced and tested under otherwise identical conditions. The test results are compiled in Table 3.

TABLE 3

| Period of exposure until initial tensile strength is halved | |
|---|---|
| Stabilizer | Exposure period |
| none | 500 h |
| from Example 12 | 1510 h |

The tapes stabilized in accordance with the invention show an outstanding retention of strength.

What is claimed is:
1. A compound of the formula I

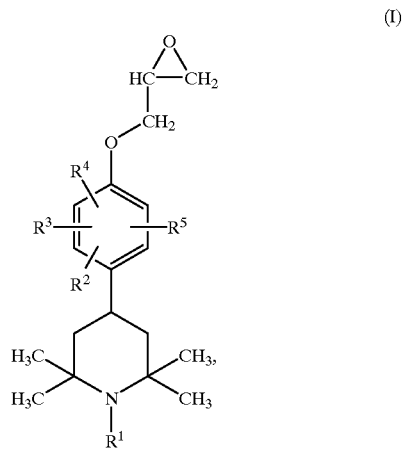

where
$R^1$ is H, $C_1$–$C_{12}$alkyl, $C_2$–$C_{12}$-alkenyl, $C_2$–$C_{12}$alkynyl, O—$C_1$–$C_{12}$alkyl, CO—$C_1$–$C_{12}$alkyl, in which radicals alkyl chains may also be interrupted by O, S, S=O, $SO_2$ or N—$C_1$–$C_{12}$alkyl, or is $C_5$–$C_{12}$cycloalkyl which is unsubstituted or substituted by
  1 to 4 $C_1$–$C_4$alkyl and/or $C_1$–$C_4$alkoxy radicals, O—$C_5$–$C_{12}$cycloalkyl, which is unsubstituted or substituted by 1 to 4 $C_1$–$C_4$alkyl and/or $C_1$–$C_4$alkoxy radicals, CO—$C_6$–$C_{14}$aryl, which is unsubstituted or substituted by 1 to 9 $C_1$–$C_4$alkyl and/or
  $C_1$–$C_4$alkoxy radicals, O-benzyl, which on the aromatic ring is unsubstituted or substituted by 1 to 4 $C_1$–$C_4$alkyl and/or $C_1$–$C_4$alkoxy radicals, CO-benzyl, which on the aromatic ring is unsubstituted or substituted by 1 to 4 $C_1$–$C_4$alkyl and/or $C_1$–$C_4$alkoxy radicals, and
$R^2$, $R^3$, $R^4$ and $R^5$ independently of one another are H, $C_1$–$C_{12}$alkyl, $C_5$–$C_{12}$cycloalkyl, O—$C_1$–$C_{12}$alkyl, O-phenyl, halogen or $NO_2$.

2. A compound according to claim 1, where
$R^1$ is H, $C_1$-$C_4$alkyl, $C_2$-$C_8$alkenyl, $C_2$-$C_4$alkynyl, O—$C_1$-$C_4$alkyl, CO—$C_1$-$C_4$alkyl or O—$C_5$-$C_6$cycloalkyl.

3. A compound according to claim 1 where
$R^1$ is H, $C_1$-$C_{12}$alkyl, $C_2$-$C_{12}$alkenyl, $C_2$-$C_{12}$alkynyl, CO—$C_1$-$C_{12}$alkyl, where alkyl chains in these radicals can also be interrupted by O, S, S=O, $SO_2$ or N—$C_1$-$C_{12}$alkyl, and
$R^2$, $R^3$, $R^4$ and $R^5$ independently of one another are H, $C_1$-$C_{12}$alkyl or O—$C_1$-$C_{12}$alkyl.

4. A compound according to claim 1, where
$R^1$ is H, $CH_3$, $CH_2$—C=CH or CO—$CH_3$ and
$R^2$, $R^3$, $R^4$ and $R^5$ independently of one another are H or $CH_3$.

5. A homopolymer, copolymer or terpolymer obtainable by addition polymerization of one or more compounds of the formula I according to claim 1.

6. A compound obtainable by reacting one or more compounds of the formula I according to claim 1 with at least one further monoglycidyl compound not of the formula I.

7. A compound obtainable by reacting one or more compounds of the formula I according to claim 1 with at least one amine or one carboxylic acid or one phenol or dicarboxylic anhydride or alcoholate.

8. A compound of the formula I according to claim 1 which is adsorbed on a filler.

9. A compound according to claim 8, where the filler is $TiO_2$, $SiO_2$, $CaCO_3$, $CaSO_4$, $BaSO_4$, $Al(OH)_3$, talc, carbon black, glass fibres or glass beads, cellulose or wood flour.

10. A composition comprising a) an organic material which is sensitive to damage by light, oxygen and/or heat and b) as stabilizer at least one compound according to claim 1.

11. A composition comprising a) an organic material which is sensitive to damage by light, oxygen and/or heat and b) as stabilizer at least one filler according to claim 8.

12. A composition according to claim 10, in which component a) is an organic polymer.

13. A composition according to claim 10, in which component a) is a synthetic polymer.

14. A composition according to claim 10, in which component a) is a polyolefin or a coating binder based on acrylic, alkyd, polyurethane, polyester or polyamide resin or appropriately modified resins.

15. A composition according to claim 10 comprising further customary additives in addition to components a) and b).

16. A composition according to claim 10 containing from 0.01 to 10% by weight of component b) based on the weight of the composition.

17. A composition according to claim 11, in which component a) is an organic polymer.

18. A composition according to claim 11, in which component a) is a synthetic polymer.

19. A composition according to claim 11, in which component a) is a polyolefin or a coating binder based on acrylic, alkyd, polyurethane, polyester or polyamide resin or appropriately modified resins.

20. A composition according to claim 11 comprising further customary additives in addition to components a) and b).

21. A composition according to claim 11 containing from 0.01 to 10% by weight of component b) based on the weight of the composition.

22. A method of stabilizing organic material against damage by light, oxygen and/or heat, which comprises admixing to said material a compound according to claim 1.

23. A method of stabilizing organic material against damage by light, oxygen and/or heat, which comprises admixing to said material a compound according to claim 1.

24. A composition comprising
(a) an organic material which is sensitive to damage by light, oxygen and/or heat, and
(b) as stabilizer at least one polymer according to claim 5.

25. A composition comprising
(a) an organic material which is sensitive to damage by light, oxygen and/or heat, and
(b) as stabilizer at least one polymer according to claim 6.

26. A composition comprising
(a) an organic material which is sensitive to damage by light, oxygen and/or heat, and
(b) as stabilizer at least one polymer according to claim 7.

27. A method of stabilizing an organic material which is sensitive to damage by light, oxygen and/or heat, which comprises
admixing to said material a polymer according to claim 5.

28. A method of stabilizing an organic material which is sensitive to damage by light, oxygen and/or heat, which comprises
admixing to said material a polymer according to claim 6.

29. A method of stabilizing an organic material which is sensitive to damage by light, oxygen and/or heat, which comprises
admixing to said material a polymer according to claim 7.

30. A method of stabilizing an organic material which is sensitive to damage by light, oxygen and/or heat, which comprises
admixing to said material a polymer according to claim 8.

* * * * *